Figure 1:
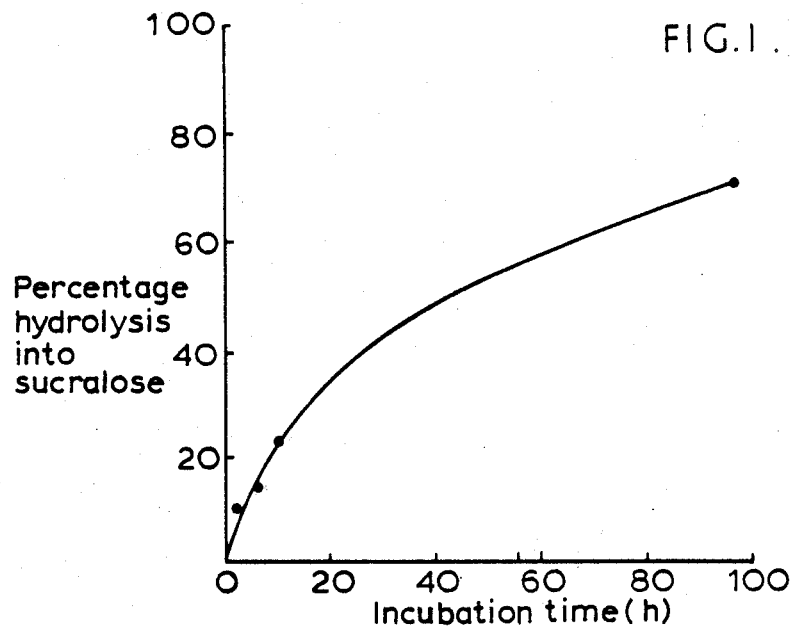

United States Patent [19]

Rathbone et al.

[11] Patent Number: 4,826,962

[45] Date of Patent: May 2, 1989

[54] TETRACHLORORAFFINOSE AND ITS USE IN THE PREPARATION OF SUCRALOSE

[75] Inventors: Elner B. Rathbone; Khizar S. Mufti; Riaz A. Khan, all of Berkshire; Peter S. J. Cheetham, Kent; Andrew J. Hacking; Jonathan S. Dordick, both of Berkshire, all of England

[73] Assignee: Tate & Lyle Public Limited Company, United Kingdom

[21] Appl. No.: 921,370

[22] Filed: Oct. 20, 1986

[30] Foreign Application Priority Data

Oct. 21, 1985 [GB] United Kingdom ............... 8525871

[51] Int. Cl.$^4$ .................... C07H 5/02; C07H 1/00
[52] U.S. Cl. .................... 536/122; 536/4.1; 536/18.4; 536/18.5; 536/124; 514/53; 514/61; 435/74; 435/100; 435/208
[58] Field of Search ............... 514/53, 61; 536/4.1, 536/18.4, 18.5, 122, 124; 435/74, 100, 208

[56] References Cited

U.S. PATENT DOCUMENTS

| | | | |
|---|---|---|---|
| 3,664,927 | 5/1972 | Shimizu et al. | 435/208 |
| 3,795,585 | 3/1974 | Suzuki et al. | 435/208 |
| 4,036,694 | 7/1977 | Meguro et al. | 435/105 |
| 4,324,888 | 4/1982 | Rathbone | 536/122 |
| 4,362,869 | 12/1982 | Jenner et al. | 536/122 |
| 4,405,654 | 9/1983 | Lee | 536/122 |

*Primary Examiner*—Ronald W. Griffin
*Assistant Examiner*—Nancy S. Carson
*Attorney, Agent, or Firm*—Ostrolenk, Faber, Gerb & Soffen

[57] ABSTRACT

The novel chlorinated sugar O-α-D-6-chloro-6-deoxygalactopyranosyl-(1→6)-α-D-4-chloro-4-deoxygalactopyranosyl-(1→2)-β-D-1,6-dichloro-1,6-dideoxyfructofuranoside (TCR) can be used to prepare sucralose by incubating the TCR in solution in the presence of an enzyme serving to remove the 6-chloro-6-deoxygalactosyl moiety from the 6-position, especially an enzyme derived from a strain of *Mortierella vinacea*, *Circinella muscae* or *Aspergillus niger*. TCR is prepared by treating raffinose with thionyl chloride in the presence of triphenylphosphine oxide.

12 Claims, 1 Drawing Sheet

TETRACHLORORAFFINOSE AND ITS USE IN THE PREPARATION OF SUCRALOSE

This invention relates to a novel tetrachlorinated derivative of raffinose and to processes for its preparation and its use in the production of the high intensity sweetener sucralose (4,1',6'-trichloro-4,1',6'-trideoxygalactosucrose also known as TGS) which is about 600X sweeter than sucrose.

Routes to sucralose (see, for example, and Khan et al Carbohydrate Research, 39 (1975) 253; Fairclough et al. Carbohydrate Research, 40 (1975) 285–298 U.S. Pat. No. 4,362,869 and GB No. 2065648) involve the formation of derivatives of sucrose in which the 6-position is blocked so as to prevent chlorination in that position while the 4-, 1'- and 6'-positions are chlorinated. In the route of U.S. Pat. No. 4,362,869 and Fairclough, sucrose is tritylated in the three primary positions (6-, 1'- and 6'-) and then peracetylated. The trityl groups are then removed to provide the 2,3,4,3',4'-pentaacetate. The acetate at the 4-position is then caused to migrate to the 6-position, in the case of the patented process by treatment with dilute acetic acid in an inert solvent, so as to provide the 2,3,6,3',4'-pentaacetate which can be chlorinated. Because the process includes the combined steps of tritylation, acetylation, detritylation and isomerisation, there is clearly a need for a simpler method of ensuring that 6-position is not chlorinated.

Another method (see, for example, U.S. Pat. No. 4,380,476 and GB No. 2079749) involves the selective acylation of the 6-position followed by the selective chlorination of the 4-, 1'- and 6'-positions in the presence of unprotected hydroxy groups at the 2-, 3-, 3'- and 4'-positions. However, the selective acylation is not easy to perform.

There thus remains a need for a simple process for the production of sucralose in a limited number of stages.

An alternative to selective 6-acylation might be to incorporate a larger group at the 6-position, for example a sugar. If such a trisaccharide is considered as a starting material, then two problems immediately present themselves.

First, the trisaccharide must be capable of being chlorinated in the 4-position (with inversion) and in the 1'-, and 6'-positions and, optionally, in positions on the sugar in the 6-position. However, the presence of a bulky sugar group at the 6-position means that the critical 4-position is sterically hindered and it would be difficult to incorporate a halogen atom.

A trisaccharide of the right type which is relatively common is raffinose, which is O-α-D-galactopyranosyl-(1→6)-O-α-D-glucopyranosyl(1→2)-β-D-fructofuranoside. The chlorination of raffinose was studied by Hough et al. (Carbohydrate Research, 71 (1979) 85–93). Using sulphuryl chloride, a potent chlorinating agent capable of chlorinating sucrose in the 4-, 6-, 1'- and 6'-positions, they found that no 4-chloro-substituted product was obtained. A mixture of mono-, di- and trisaccharides was obtained together, surprisingly, with some chlorinated methyl glycosides.

Our own studies have shown that reaction of raffinose with a Vilsmeier reagent also produced a complex mixture of reaction products.

The second problem is that, even if a suitably 4,1',6'-chlorinated trisaccharide could be obtained, it would be necessary to find some effective chemical or enzymatic way of removing the sugar from the 6-position to liberate sucralose. However, chlorination of the molecule renders it very different in polarity, configuration and, especially, conformation from the unchlorinated sugar on which an enzyme is adapted to act. This means that enzymes which act on raffinose to remove the galactose ring will not necessarily work on a chlorinated derivative of raffinose in which a chlorine substituent is present in a position close to the glycosidic bond (i.e. at the 4-position). An analogy to this is the difference between sucrose and sucralose. A number of microorganisms are able to cleave sucrose rapidly, but sucralose is not degraded in vivo although it is slowly degraded by some soil microorganisms.

Thus, the requirements for this approach to the production of sucralose to be viable are that the trisaccharide must be chlorinated in only the 4, 1'- and 6'-positions of the sucrose moiety and possibly in one or more positions of the third ring, and that the chlorinated product must be cleaved only at the (1→6)-galactosyl link without cleavage of the chlorinated galactosucrose or dechlorination of that moiety.

Surprisingly, we have now found how to chlorinate raffinose to obtain a 6-O-(6-chloro-6-deoxygalactose)-substituted sucralose. Furthermore, we have found enzymes which will cleave this tetrachloro sugar to liberate sucralose.

According to one aspect of the present invention, we provide the novel tetrachlororaffinose, namely O-α-D-6-chloro-6-deoxygalactopyranosyl-(1→6)α-D-4-chloro-4-deoxygalactopyranosyl-(1→2)-β-D-1,6-dichloro-1,6-dideoxyfructofuranoside, or 4,1',6',6''-tetrachloro-4,1',6',6''-tetradeoxygalactoraffinose, as a novel compound. This compound will also be referred to herein by the abbreviation TCR.

We also provide a process for the preparation of TCR comprising reacting raffinose with thionyl chloride in the presence of a triarylphosphine oxide e.g. triphenylphosphine oxide.

The triphenylphosphine oxide (TPPO) is preferably accompanied by a proportion of triphenylphosphine (TPP), for example by use of a mixture of from 5 to 25 mol%, e.g. 7.5 to 15%, TPP and 95 to 75 mol% e.g. 92.5 to 85%, TPPO. TPP itself can also be used, since the by-product of the TPP/thionyl chloride chlorinating agent is TPPO. This means that as the reaction proceeds, a mixture of TPPO and TPP is generated.

Other triarylphosphine oxides can be substituted for TPPO, especially those in which one of the three phenyl rings is attached to a polymeric chain, for example the reagents described by Regen and Lee (J. Org. Chem. 40 1669–1670, 1975) where phenyl is replaced by styrene.

Similarly, the TPPO can be replaced by the sulphide (TPPS), which reacts similarly.

The ratio of triarylphosphine/triarylphosphine oxide or sulphide to raffinose is preferably 3 to 4 mols per mol, e.g. about 3.2 mols per mol, and the ratio of thionyl chloride to raffinose is preferably 8 to 15 mols per mol, e.g. 10 to 11 mols per mol.

The reaction proceeds in the presence of a non-hydroxylic solvent for the raffinose and the chlorinating reagents. Suitable solvents include amines and amides, especially aromatic tertiary amines such as pyridine and lutidine, or N,N-dialkylamides such as DMF.

The reaction is conveniently initiated at about 0° which is subsequently raised generally to about 110°.

The TCR is conveniently isolated in the form of the heptaester, e.g. the heptaacetate, and then the ester groups are removed by hydrolysis, e.g. with dilute alcoholic sodium alkoxide.

According to a further feature of the present invention, we also provide a process for the production of sucralose comprising incubating a solution of TCR in the presence of an enzyme serving to remove the 6-chloro-6-deoxy-galactosyl moiety from the 6-position.

The enzyme may be selected from among the very many enzymes available, either directly or by the culture of microorganisms capable of producing the enzymes. Galactosidases are of particular interest, although melibiases might be considered of less interest in view of the fact that although melibiose (O-α-D-galactopyranosyl-(1→6)-α-D-glucopyranose) is a component of raffinose, the chlorinated TCR has an inverted configuration. We find that many of those enzymes do not have any useful activity on TCR, even though they are capable of releasing sucrose from raffinose. Some 20 α-galactosidase enzymes from bacterial, fungal and plant sources were tested, but only 8 exhibited any activity in hydrolyzing TCR, all from fungi. The most active enzymes were from strains of *Mortierella vinacea*, *Circinella museae* and from one strain of *Aspergillus niger* (supplied by Novo A/S). Surprisingly the melibiase derived from *Mortierella vinacea* var *raffinoseutilizer* (ATCC 20034), supplied by Hokkaido Sugar Co. was the most active. Even so, the rate of reaction on TCR is only a few percent of the rate on raffinose itself. Nevertheless, considering the significant conformational and configurational differences between raffinose and TCR, even this rate of activity is unexpected and led to virtually complete hydrolysis of TCR to sucralose.

Pelletised cells of *M. vinacea* var. *raffinoseutilizer* have been used since 1968 in the processing of beet sugar in Japan and formerly in the USA (Obara J. & Hashimoto S., Sugar Technology Reviews 4, 209, 1976/77 and U.S. Pat. Nos. 3,867,256 and 3,957,578 to Narita et al.).

The enzyme treatment is conveniently effected in aqueous solution, but although the reaction needs water we have discovered that α-galactosidase can vigorously hydroyze TCR to sucralose in a number of organic solvents. Thus, we have found that the enzyme is most stable and active in water-immiscible organic solvents, while TCR is highly soluble only in hydrophilic solvents. Therefore, hydrophilic yet water-immiscible organic solvents such as ethyl acetate, n-butanol, and methyl isobutyl ketone were deemed the most appropriate solvents for TCR hydrolysis. For example, the rate of TCR hydrolysis as defined by the catalytic turnover number ($K_{cat}$) in ethyl acetate pre-saturated with aqueous buffer (which provides enough water for hydrolysis) is similar to that in aqueous buffer. This suggests that the enzyme retains its full catalytic activity, even when suspended in an organic solvent. It is important to stress that each organic solvent, while pre-saturated with aqueous buffer, remains as a single organic phase. We are not dealing with a biphasic solvent system and the enzyme is functioning in the organic phase.

In addition to the solvents mentioned above, several other solvents were investigated for their abilities to support TCR hydrolysis. Highly water-miscible solvents (e.g. dioxane, acetone, methanol, and THF) were unable to support hydrolysis even in the presence of 30% v/v aqueous buffer. Hydrophobic, water-immiscible solvents (e.g. n-octanol, nitrobenzene, and butyronitrile) were able to support TCR hydrolysis, but the poor solubility of TCR in these solvents (less than 5% w/v) limits the practicality of using them on a large scale. The hydrophilic, water-immiscible solvents (e.g., ethyl acetate, n-butanol, and methyl isobutyl ketone) were able to support high catalytic activity and high TCR solubility.

Table 1 shows the solubility of both TCR and sucralose at 55° C. in various solvents (all pre-saturated with aqueous buffer) as compared to aqueous buffer.

TABLE 1

| Solvent | TCR | Sucralose |
| --- | --- | --- |
| water | 15% | 30% |
| n-butanol | >50% | >50% |
| methyl isobutyl ketone | >50% | 6% |
| ethyl acetate | >50% | 5.7% |
| n-octanol | 5% | <1% |
| nitrobenzene | <2% | <1% |

Clearly, TCR solubility was maximised in the hydrophilic water-immiscible solvents. On the other hand, much variability in sucralose solubility was found. This may be used to crystallise sucralose selectively in ethyl acetate or methyl isobutyl ketone for batch reactions or to enable to continuous packed-bed process to be run in n-butanol (all reactants and products soluble).

Among the advantages for carrying out the hydrolysis reaction in organic media are enhanced thermal stability (the stability of α-galactosidase at 55° C. in ethyl acetate is nearly 50% higher than in aqueous solution) and increased substrate solubility (the solubility of TCR in the above-mentioned solvents is greater than 50% w/v whereas in aqueous buffer the solubility is only 15% w/v).

In both aqueous and organic systems, the treatment should naturally be at the optimum temperature and pH for the enzyme which, for the *M. vinacea* melibiase is about 55° C. and pH 4.5–5.5. In water-saturated organic solvents this refers to the pH of the aqueous buffer. At this temperature and at a pH of 5.0, we find that the sucralose produced is not degraded.

The enzyme may be dissolved or dispersed in the aqueous system as a cell-free extract produced e.g. by sonication of the pellets, or may be used in the immobilised form, for example as pellets packed into beds or columns. In the organic systems, the enzyme remains in the insoluble form and again can be used in beds or columns.

The separation of the sucralose product may be achieved by any convenient steps, for example by evaporation and extraction into an organic solvent, by chromatographic techniques, or by selective crystallisation from either the aqueous or the non-aqueous systems.

The following examples illustrate the invention further:

EXAMPLE 1

(a)
4,1',6',6"-Tetrachloro-4,1',6',6"-tetradeoxygalactoraffinose heptaacetate

To a cooled solution of anhydrous raffinose (4.0 g), triphenylphosphine oxide (5.9 g) and triphenylphoshine (0.66 g, 10% by weight of TPPO, total TPPO and TPP 3 mol. equiv.) in pyridine (40 ml) at about 0° C., was added thionyl chloride (8.6 ml, 15 mol. equiv.) with stirring. The reaction mixture was brought to ambient temperature over a period of 1 hour and then heated at 105°–110° C. for 4.5 hours. After addition of methanol (10 ml), the solution was then concentrated to a syrup.

A solution of the syrup in pyridine (50 ml) was treated with acetic anhydride (5 ml) at room temperature for 2 hours. T.l.c. (ether-acetone, 4:1) showed a fast-moving minor and a slow-moving major product. The solution was concentrated and eluted through a column of silica gel using ether-acetone (2:1, v/v) to give 4,1',6',6''-tetrachloro-4,1',6',6''-tetradeoxygalactoraffinose heptaacetate (4.75 g) as a syrup. The sample showed the presence of TPPO and some slower-moving impurities, according to t.l.c.

(b)
4,1',6',6''-Tetrachloro-4,1',6'-6''-tetradeoxygalactoraffinose

The above syrup (4.75 g) was deesterified using sodium methoxide in methanol (50 ml) at pH 9.5 at room temperature for 3 hr. The solution was neutralised with Amberlyst 15 (H)+ resin, concentrated to give a semi-solid residue, and was extracted with water. The insoluble TPPO was removed by filtration and the water extract was purified by elution through a column of silica gel (100 g) using ethyl acetate-acetone (2:1, v/v) to give pure 4,1',6',6''-tetrachloro-4,1',6',6''-tetradeoxygalactoraffinose (1.49 g, 32.6% based on raffinose), $[\alpha]_D + 80°$ (c 0.7, acetone).

Conventional acetylation of the product with acetic anhydride and pyridine afforded the peracetate of step (a), $[\alpha]_D + 132°$ (c 0.25, acetone).

Mass spectral data for heptaacetate: m/z, 753, $[(M+1)^+ -2AcOH$, octet, (4Cl)], 571 [4-chlorogalactopyranosyl-(1→6)-4-chlorogalactopyranosyl cations, triplet 9:6:1 (2Cl)], 307 [6-chlorogalactopyranosyl cation, doublet 3:1, (1Cl)], 283 [1,6-dichlorofructofuranosyl cation, triplet 9:6:1 (2 Cl)].

Mass spectral data for TCR: m/z 596 [M+NH$_4$, octet, 4Cl], 396 and 398 (overlapping peaks) [6-chlorogalactopyranosyl-(1→6)-4-chlorogalactopyranosyl cation (2Cl); 1,6-dichlorofructosyl-(2→1)-4-chlorogalactopyranosyl cation (3Cl)], 198 [6-chlorogalactopyranosyl+NH$_4$, doublet (3:1) (1Cl)].

$^1$H—n.m.r. data for 4,1',6',6''-tetrachloro-4,1',6',6'' tetradeoxygalactoraffinose heptaacetate

| Proton | Chemical Shift (τ) | Coupling Constant (Hz) |
|---|---|---|
| H-1 | 5.68 | d, J$_{1,2}$ 3.5 |
| H-2 | 5.08 | q, J$_{2,3}$ 10.0 |
| H-3 | 5.41 | q, J$_{3,4}$ 3.5 |
| H-4 | 4.76 | q, J$_{4,5}$ 1.5 |
| H-5 | 4.57 | — |
| H-1'a, 1'b | 4.04 | — |
| H-3' | 5.41 | d, J$_{3',4'}$ 6.5 |
| H-4' | 5.34 | t, J$_{4',5'}$ 6.5 |
| H-5' | 4.27 | m |
| H-1'' | 5.43 | d, J$_{1'',2''}$ 3.5 |
| H-2'' | 5.16 | q, J$_{2'',3''}$ 11.0 |
| H-3'' | 4.94 | q, J$_{2'',3''}$ 3.5 |
| H-4'' | 5.01 | — |
| Acetate H | 1.92, 2.03, 2.04, 2.05, 2.06, 2.07 | s |

$^{13}$C—n.m.r. data for 4,1',6',6''-tetrachloro-4,1',6',6''-tetradeoxygalactoraffinose

| Carbon | Chemical Shift (τ) |
|---|---|
| C-2' | 103.05 |
| C-1'' | 99.81 |
| C-1 | 92.31 |
| C-5' | 82.40 |
| C-3' | 75.89 |
| C-4' | 75.40 |
| C-5'' | 71.17 |
| C-3'' | 69.12 |
| C-4'' | 69.04 |
| C-2'' | 68.24 |
| C-2,3,5 | 67.88, 67.40, 67.32 |
| C-6 | 67.04 |
| C-4 | 65.42 |
| C-1' | 46.35 |
| C-6' | 44.12 |

EXAMPLE 2

Isolation of TCR via 4,1',6',6''-tetrachlororaffinose heptaacetate

In a solution of anhydrous raffinose (10 g, 19.8 mmol) in pyridine (35 ml, 434 mmol) was dissolved triphenylphosphine oxide (16 g, 57.5 mmol) and triphenylphosphine (1.6 g, 6.1 mmol) by warming and stirring. Thionyl chloride (15 ml, 207 mmol) was then added to the mixture at 0° C. (ice-salt bath) over a period of 30 min. The reaction mixture was brought to room temperature (if stirred, an exotherm could be experienced). The reaction mixture was then heated at 105°–110° C. Within 5 min. the exotherm began and the internal temperature rose to 150° C. The temperature then came down to the bath temperature within 0.5 h. The heating was continued for 4.5 h. The solution was then brought to room temperature and treated with excess of acetic anhydride (about 25 ml) at room temperature with stirring for 24 h. Alternatively, the acetylation reaction time can be reduced by 1 h by carrying out the reaction at 100° C.

The product was isolated by extracting the mixture with hot toluene. The toluene layer was washed with aqueous sodium carbonate, water, dried (Na$_2$SO$_4$), and the filtrate concentrated. The toluene extract contained 26 g of solids comprising a mixture of carbohydrate and triphenylphosphine oxide. The black residue was further stirred with toluene and aqueous sodium carbonate, the black solid residue was filtered off, to give a second toluene extract which was separated, dried (Na$_2$SO$_4$), and concentrated (4 g solids). Diethyl ether was added to the combined extracts to precipitate out the triphenyl-phosphine oxide (15 g). The ether extract was concentrated to a syrup (about 15 g), taken up in methanol (about 100 ml) and treated with 1M sodium methoxide (pH 10) for 2 h. The solution was neutralised with an acidic resin and filtered through a bed of charcoal. The solution was concentrated and dried in a vacuum oven at 40° C. for 24 h (10.8 g). The residue was then extracted with water, the residual TPP=O filtered off, and the filtrate concentrated to give TCR (5.3 g). T.l.c. (ethyl acetate:acetone:water, 8:6:1) showed that approximately 80% of the carbohydrate present was TCR.

EXAMPLE 3

Direct Isolation of TCR

A solution of anhydrous raffinose (20 g, 39.7 mmol) in pyridine (70 ml, 868 mmol) was treated with triphenylphosphine oxide (32 g, 115 mmol), triphenylphosphine (3.2 g, 12.2 mmol) and thionyl chloride (30 ml, 414 mmol) as described in the preceding Example. The reaction mixture was brought to room temperature and then heated at 105°–110° C. for about 4.5 h. Methyl isobutyl ketone (MIBK, 300 ml) was then added to the hot (about 70°) reaction mixture, stirred, and the MIBK layer decanted. The black residue was further extracted with hot (about 70° C.) MIBK (100 ml). The combined MIBK extracts were washed with cold aqueous sodium carbonate, dried (CaSO$_4$), and concentrated to a syrup. The syrup was taken up in methanol (50 ml) and treated with sodium methoxide (pH 10) at room temperature for about 1 h in order to give TCR. T.l.c (ethyl acetate:acetone:water, 8:6:1) showed a major product which was coincident with the standard TCR. The methanol solution was deionised with acidic resin, decolorised with activated charcoal, filtered, and the filtrate concentrated to a solid residue. The residue was stirred with hot water, filtered, and the filtrate concentrated to give solid TCR (9.8 g of 60.6% purity HPLC, yield 26%).

EXAMPLE 4

Preparation of sucralose (Small scale) in aqueous solution

The tetrachlorogalactoraffinose of Example 1 (20 mg) was placed in a screw-top bottle together with 0.1M-citrate-phosphate buffer (pH 5.0) (2 ml) to give a 1% (w/v) solution. This level of water was maintained during the following incubation period by addition of more water when required.

Melibiase in the form of pelletised cells of *Mortierella vinacea* var *raffinoseutilizer* (ATCC 20034) (supplied by Hokkaido Sugar Co, Japan) was added (10 mg) and the mixture was incubated at 55° C. for up to 100 hours. The degree of hydrolysis was followed periodically by t.l.c. analysis of withdrawn 250 μl aliquots eluted with ethyl acetate:ethanol:water (45:5:1) or by hplc on a Waters Dextropak C18 reverse phase column eluted by acetonitrile 20% (v/v) and products measured using a refractive index detector. The result is plotted in FIG. 1. It was found, for example, that about 53% had been hydrolysed after 48 hours and about 70% after 90 hours. The products were separated by chromatography and, in addition to sucralose, the presence of 6-chlorogalactose and TCR was detected. TCR can be used at up to 15% (w/v) in this system. In aqueous solution, the enzyme has a Michaelis constant ($K_m$) of 5.8 Mm and a $K_{cat}$ of 52.5 mg per g enzyme per hour.

EXAMPLE 5

Pellets of *Mortierella vinacea* var *raffinoseutilizer* (ATCC 20034) (3 g) were hydrated in a solution of 0.1M citrate phosphate buffer pH 5.0 containing raffinose 5% w/v and were packed in a column 11 cm×0.9 cm and bed volume 7 cm$^3$ with a water jacket. This column was maintained at 55° C. using a circulating water pump. When used to hydrolyse TCR to sucralose, the half life of the column for 50% conversion was found to be 13 days.

EXAMPLE 6

Organisms capable of hydrolysing TCR to sucralose

Organisms reported to have an α-galactosidase activity were obtained from the ATCC. They were grown in 500 ml shake flasks containing 100 ml of a mineral salts medium (Jayasuria, 1955 Journal of General Microbiology 12 419–428) containing 1 g/l yeast extract plus 5 g/l raffinose at 30° C. Cells were collected by centrifugation (5000 rev/min for 10 min) in the late exponential phase of growth, resuspended in 5 times their volume of citrate-phosphate buffer pH 5.0, and maintained at 0° C. in an ice bath and were disrupted by 3×20 second bursts in a MSE sonicator (Dawe Soniprobe Type 1130A) at maximum output. The resulting suspension was centrifuged (17,000 rev/min) for 30 minutes and both debris and supernatant assayed for α-galactosidase activity in units per g. dry weight of cell debris using p-nitrophenyl α-D-galactopyranoside (Sigma). Virtually no enzyme activity was detected in the supernatant. Cultures which were positive were then tested for TCR hydrolysis as in Example 4 and the results given in mg sucralose per g dry weight of cell debris per hour (for 70% conversion). The results were as follows:

| Organism | ATCC No | Enzyme Units | TCR Hydrolysis |
|---|---|---|---|
| *Absidia griseola* | 20430 | 35.5 | 0 |
| *Absidia griseola* | 20431 | 18.6 | <0.2 |
| *Absidia griseola* | 22618 | 43.7 | 0 |
| *Aspergillus awamori* | 44733 | 20.8 | 0 |
| *Aspergillus niger* | 36220 | 20.1 | 0.49 |
| *Circinella muscae* | 16008 | 75.4 | 1.12 |
| *Circinella muscae* | 20394 | 28.9 | <0.2 |
| *Circinella muscae* | 22337 | 11.3 | 0 |
| *Mortierella vinacea* | 20034 | 18.2 | 1.09 |
| *Mortierella vinacea* | 34195 | 8.9 | 1.33 |
| *Mortierella vinacea* | 42425 | 10.6 | 1.06 |
| *Saccharomyces uvarum* | 42367 | 1.6 | 0 |
| *Talaromyces thermophilus* | 16461 | <1.0 | 0 |
| *Mortierella vinacea* | Hokkaido (pellets) | 21.3 | 4.3 |

EXAMPLE 7

Production of sucralose in organic media

Figure 2:
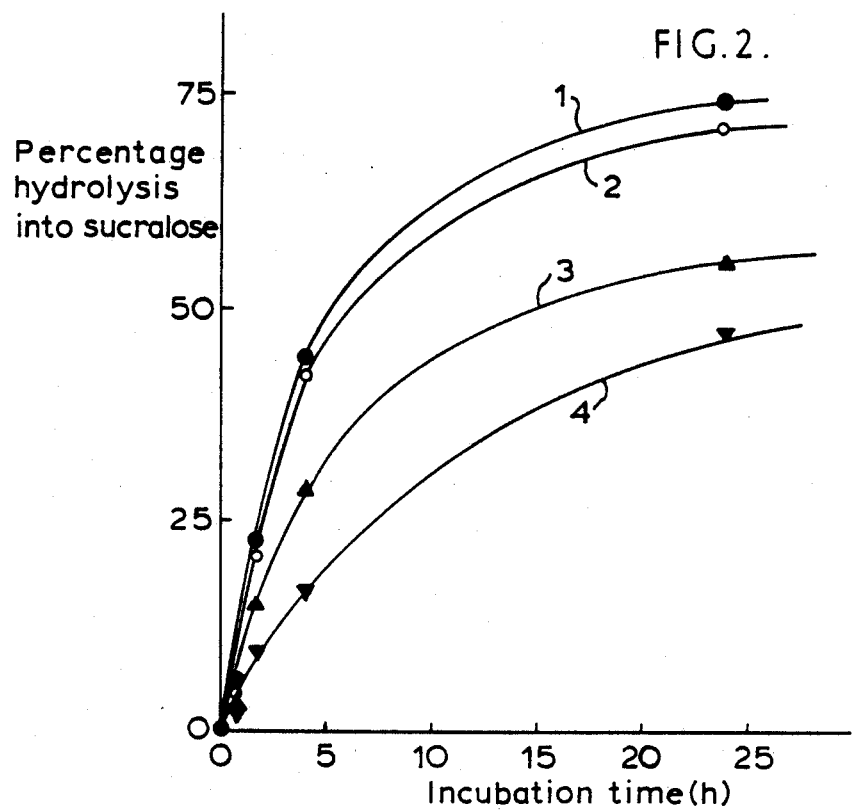

The TCR of Example 1 (23 mg) was placed in a 5 ml screw-top vial and 2 ml of an organic solvent which had been pre-saturated with aqueous buffer (sodium acetate, 50 mM, pH 5.0) was added to give a 20 mM (1.15% w/v) solution. α-Galactosidase in the form of pelletized cells of *M. vinacea* var *raffinoseutilizer* (ATCC 20034) was added (100 mg) to each vial and the reactions were initiated by adding 1% v/v aqueous buffer, vortexing for 30 seconds, and placing the vial in a water-bath shaker at 55° C. and 100 rpm. Periodically, aliquots were removed and 25 μl were injected into an Hplc system fitted with a reverse phase (Waters Dextropak C18) column, using 20% aqueous acetonitrile as eluant, to measure the sucralose produced and the residual TCR. The effect of the organic solvent on the production of sucralose during a 24 hour incubation is shown in FIG. 2. In the figure the progress of the hydrolysis of TCR into sucralose with time is plotted for aqueous buffer (curve 1) and for three solvents, methyl isobutyl ketone (2), ethyl acetate (3) and n-butanol (4). The hydrolysis reaction in methyl isobutyl ketone and in aqueous buffer were similar. Lower rates and conversions were obtained in ethyl acetate and n-butanol, respectively. In all cases, greater than 50% conversion in 24 hours was observed, with 70% conversions in aqueous buffer and methyl isobutyl ketone.

In a spearate experiment, the enzyme exhibited Michaelis-Menten kinetics in both aqueous buffer and ethyl acetate. The $K_m$ and $K_{cat}$ in ethyl acetate were 16.4 mM TCR and 56.3 mg sucralose/g pellets/h, respectively. The reason that the time-course for TCR hydrolysis in ethyl acetate was lower than that in aqueous buffer at 20 mM TCR was due to the higher $K_m$ of TCR in ethyl acetate and not due to a lower catalytic activity. When 50 mM TCR was used, the rates and conversions of TCR hydrolysis in ethyl acetate were similar to those in aqueous buffer.

We claim:

1. O-α-D-6-chloro-6-deoxygalactopyranosyl-(1→6)-α-D-4-chloro-4-deoxygalactopyranosyl-(1→2)-β-D-1,6-dichloro-1,6-dideoxyfructofuranoside.

2. A process for the production of sucralose comprising enzymatically removing the 6-chloro-6-deoxygalactosyl moiety from the 6-position of O-α-D-6-chloro-6-deoxygalactopyranosyl-(1→6)-α-D-4-chloro-4-deoxygalactopyranosyl-(1→2)-β-D-1,6-dichloro-1,6-dideoxyfructofuranoside.

3. The process according to claim 2, in which the enzyme is derived from a strain of *Mortierella vinacea*, *Circinella muscae* or *Aspergillus niger*.

4. The process according to claim 3, in which the enzyme is derived from *Mortierella vinacea* var. *raffinoseutilizer*.

5. The process according to claim 2, in which the O-α-D-6-chloro-6-deoxygalactopyranosyl-(1→6)-α-D-4-chloro-4-deoxgalactopyranosyl-(1→2)-β-D-1,6-dichloro-1,6-dideoxyfructofuranoside is dissolved in an aqueous solution or in a water-immiscible hydrophilic organic solvent.

6. The process according to claim 5, in which the solvent is selected from the group consisting of methyl isobutyl ketone, ethyl acetate and n-butanol.

7. The process according to claim 2, effected at a temperature of about 55° C. and a pH of 4.5 to 5.5.

8. A process for the production of O-α-D-6-chloro-6-deoxygalactopyranosyl-(1→6)-α-D-4-chloro-4-deoxygalactopyranosyl-(1→2)-β-D-1,6-dichloro-1,6-dideoxyfructofuranoside comprising reacting raffinose with thionyl chloride in the presence of a reagent selected from the group consisting of a triarylphosphine oxide and a triarylphosphine sulphide.

9. The process of claim 8, wherein the reagent is selected from the group consisting of triphenyl phosphine oxide and triphenyl phosphine sulphide.

10. The process of claim 9 conducted in the further presence of triphenylphosphine.

11. The process of claim 10 in which the ratio of reagent to raffinose is 3–4 mol per mol and the ratio of thionyl chloride to raffinose is 8–15 mos per mol.

12. The process of claim 8 in which the ratio of reagent to raffinose is 3–4 mol per mol and the ratio of thionyl chloride to raffinose is 8–15 mol per mol.

* * * * *